United States Patent [19]

Künzle

[11] 4,061,752
[45] Dec. 6, 1977

[54] 6-PIPERAZINO-11-METHYLENE-DIBENZAZEPINES[b,E]

[75] Inventor: Franz Martin Künzle, Bern, Switzerland

[73] Assignee: Sandoz Ltd., Basel, Switzerland

[21] Appl. No.: 710,122

[22] Filed: July 30, 1976

[30] Foreign Application Priority Data

Aug. 6, 1975  Switzerland ............ 10247/75
Sept. 11, 1975  Switzerland ............ 11810/75
Jan. 13, 1976  Switzerland ............ 319/76

[51] Int. Cl.² ............ A61K 31/495; C07D 403/04
[52] U.S. Cl. ............ 424/250; 260/268 TR
[58] Field of Search ............ 260/268 TR; 424/250

[56] References Cited

FOREIGN PATENT DOCUMENTS 1,105,230  3/1968  United Kingdom.

OTHER PUBLICATIONS

S. R. Allen et al., Chemical Abstracts, vol. 79, p. 121, 977p (1973).

Primary Examiner—Donald G. Daus
Assistant Examiner—Jose Tovar
Attorney, Agent, or Firm—Gerald D. Sharkin; Robert S. Honor; Thomas O. McGovern

[57] ABSTRACT

This invention provides new compounds of formula I,

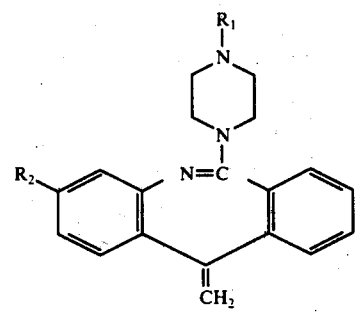

wherein
$R_1$ is hydrogen, alkyl of 1 to 4 carbon atoms, or hydroxyalkyl of 1 to 4 carbon atoms, and
$R_2$ is hydrogen or halogen, useful as anti-psychotics and sleep-inducing agents.

12 Claims, No Drawings

6-PIPERAZINO-11-METHYLENE-DIBENZAZEPINES[b,E]

The present invention relates to morphanthridine derivatives.

The present invention provides compounds of formula I,

[Structure I: piperazine with $R_1$ on N, attached via N=C to dibenzazepine ring with $R_2$ substituent and $CH_2$ group]

wherein $R_1$ is hydrogen, alkyl of 1 to 4 carbon atoms, or hydroxyalkyl of 1 to 4 carbon atoms, and $R_2$ is hydrogen or halogen.

When $R_1$ is alkyl, it is preferably methyl. When $R_1$ is hydroxyalkyl, this preferably has 2 to 4 carbon atoms. The hydroxy group is preferably bound to the terminal carbon atom away from the nitrogen atom to which $R_1$ is bound. $R_1$ is, for example, β-hydroxyethyl. $R_1$ is preferably hydrogen or alkyl.

When $R_2$ is halogen, it is fluorine, chlorine or bromine, especially fluorine or chlorine.

The present invention also provides a process for the production of a compound of formula I, as defined above, which comprises reacting a compound of formula II,

[Structure II: dibenzazepine with $R_2$ substituent, N=C with X group, and $CH_2$]

wherein $R_2$ is as defined above, and

X is a group capable of being split off with a hydrogen atom bound to the nitrogen atom of a secondary amine, with a compound of formula III,

[Structure III: H—N piperazine N—$R_1$]

wherein $R_1$ is as defined above.

The process may be effected in known manner for such condensations.

In the compound of formula II, X is preferably halogen, especially chlorine. Alternatively X is an amino group which is optionally substituted by one or two alkyl groups, sulfhydryl, alkoxy or alkylthio of 1 to 5 carbon atoms, for example, methoxy or methylthio, p-nitrobenzylthio, or tosyloxy.

The reaction may be conveniently effected in an inert organic solvent, for example, xylene or dioxane, at temperatures between 50° and 170° C, preferably between 100° and 140° C.

When X is an optionally substituted amino group the reaction may conveniently be effected in the presence of a catalytic amount of an acid, for example, p-toluenesulphonic acid or sulphuric acid. Alternatively an acid addition salt of a compound of formula II may be used.

The resulting compounds of formula I may be isolated and purified in conventional manner.

A compound of formula II, used as starting material may be obtained by a. reacting a compound of formula IV,

[Structure IV: $R_2$-substituted aryl with NH—CO linkage and C=O group]

wherein $R_2$ is as defined above, with a compound of formula V, $$CH_3-MgY \quad V$$

wherein Y is chlorine, bromine or iodine, especially bromine, under conventional conditions for a Grignard reaction, b. hydrolysing the resulting reaction complex to give a 11-methyl-11-hydroxy reaction product, c. dehydrating the 11-methyl-11-hydroxy reaction product in conventional manner to give a compound of formula VI,

[Structure VI: $R_2$-substituted aryl with NH—CO linkage and $CH_2$ group]

wherein $R_2$ is as defined above, and d. converting the compound of formula VI in conventional manner into a compound of formula II, wherein X is halogen, which may be optionally converted into compounds of formula II, wherein X is defined above but is other than halogen.

Insofar as the preparation of any starting material is not particularly described, this is known or may be produced and purified in known manner or in analogous manner to methods described herein or in analogous manner to known processes.

Free base forms of compounds of formula I may be converted into acid addition salt form in conventional manner and vice versa. Suitable acids for salt formation include hydrochloric acid, methane-sulphonic acid or maleic acid.

In the following Examples all temperatures are uncorrected and are in degrees Centigrade.

EXAMPLE 1:

11-Methylene-6-(4-methylpiperazin-1-yl)-morphanthridine a. 6-Chloro-11-methylene-morphanthridine 8 g of 5,6-dihydro-11-methylene-morphanthridin-6-one are boiled for 2 hours with 3 ml of N,N-dimethylaniline and 80 ml of phosphoryl chloride. The resulting dark solution is concentrated in a vacuum. The residue is treated with xylene and once again the mixture is evaporated in a vacuum. The residue is dissolved in 80 ml of xylene and the solution is poured onto ice-water. The mixture is extracted twice with xylene. The xylene extracts are combined, washed in turn with dilute hydrochloric acid, water and a saturated sodium chloride aqueous solution, dried over sodium sulphate and treated with active charcoal. The xylene solution is filtered through aluminum oxide and concentrated to a volume of about 100 to 150 ml in a vacuum. This solution contains 6-chloro-11-methylene-morphanthridine which is used directly in step (b).

b.
11-Methylene-6-(4-methylpiperazin-1-yl)-morphanthridine

The xylene solution of 6-chloro-11-methylene-morphanthridine is treated with 8 g of N-methylpiperazine and the mixture is boiled for 4 hours. The hydrochloride salt of N-methylpiperazine precipitates out of solution. The mixture is treated with water and 25 ml of a concentrated sodium hydroxide aqueous solution. The organic phase is shaken twice with ether, washed with water and extracted with 2N hydrochloric acid.

The acid extract is made alkaline with 2N aqueous sodium hydroxide solution and the resulting oily phase which separates out is extracted twice with ether. The ether extracts are combined, washed with water and a saturated aqueous sodium chloride solution, dried over sodium sulphate, treated with active charcoal and then filtered through aluminium oxide. Recrystallization from ether/petroleum ether yields 11-methylene-6-(4-methylpiperazin-1-yl)-morphanthridine as prisms; M.Pt. 119° – 120°.

In analogous manner to that described in Example 1 using the appropriate starting materials of formulae II and III the following compounds of formula I are obtained, wherein:

| Ex.No. | $R_1$ | $R_2$ | M.Pt. |
|---|---|---|---|
| 2 | H | H | 190–195° C[1)2)] / 208–211° C[1)3)] |
| 3 | HO—CH$_2$—CH$_2$— | H | 151–155° C[2)] |
| 4 | HO—CH$_2$—CH$_2$— | Cl | 147–149° C |
| 5 | H | Cl | 130–138° C[2)] |
| 6 | CH$_3$ | Cl | 162–164° C |
| 7 | H | F | 125–126° C |
| 8 | CH$_3$ | F | 138–140° C |

[1)]decomposition
[2)]maleate salt form.
[3)]methane sulphonate salt form

The production of the 5,6-dihydro-3-halo-11-methylene-morphanthridin-6-ones used as starting materials of formula IV may be effected as follows:

a. 5,6-dihydro-3-fluoro-morphanthridin-6,11-dione

A solution of 88 g of chromium (VI) trioxide in 60 ml of water is added dropwise over 4 hours to a stirred solution of 5,6-dihydro-3-fluoro-morphanthridin-6-one in 1.5 liters of acetic acid warmed to 60° C. The mixture is then heated for 1 hour under reflux, cooled and then poured onto ice-water. The crystals formed are separated off and washed with water. After drying the heading compound M.Pt. 282°–285° C (sublimation) is obtained.

In analogous manner 3-chloro-5,6-dihydro-morphanthridin-6,11-dione is obtained, melting at 293°–295° C.

b.
5,6-Dihydro-3-fluoro-11-methylene-morphanthridin-6-one 150 ml of absolute tetrahydrofuran is added in portions with an exothermic reaction to a Grignard solution of 5.6 g of magnesium, 30.6 g of methyl iodide and 80 ml of ether. The solution is cooled to 10° C. In a nitrogen gas atmosphere this solution is treated in small portions with a suspension of 19 g of 5,6-dihydro-3-fluoro-morphanthridin-6,11-dione in 200 ml of absolute tetrahydrofuran. The mixture is stirred for 4 hours at room temperature and then poured onto an ice-cold ammonical ammonium chloride aqueous solution. The mixture is then extracted with ether. The ether extracts are washed with brine and concentrated to dryness. The hard residue containing 5,6-dihydro-3-fluoro-11-hydroxy-11-methyl-morphanthridin-6-one is dissolved in a little acetone, treated with 18 g of pyridine hydrochloride and warmed in the presence of a stream of nitrogen. After the acetone is removed, the mixture is warmed for 90 minutes to 130° – 140° C, cooled somewhat, treated with water, separated from the water and dried. After recrystallization from acetone/petroleum ether the heading compound melting at 220° – 230° C (crystal change from 160° C) is obtained.

In analogous manner 3-chloro-5,6-dihydro-11-methylene-morphanthridin-6-one melting at 247° – 249° C is obtained.

The compounds of formula I are useful because they possess pharmacological activity in animals. In particular, the compounds are useful as anti-psychotics and neuroleptics, e.g. for the treatment of neuroses and psychoses in animals as indicated by standard tests in animals. For example the compounds inhibit the spontaneous locomotor activity of mice on administration p.o. of from about 1 to about 50 mg/kg animal body weight of the compounds using the method of Caviezel and Baillod (Pharma Acta Helv. 33, 465–484 [1958]). Additionally, the compounds inhibit the arousal reaction in rabbits on administration i.v. of from about 1 to about 5 mg/kg animal body weight of the compounds using the method of Stille et al (Int. J. Neuropharmacology 4, 375–391 [1965]).

For the above mentioned use the dosage will, of course, vary depending on the compound employed, mode of administration and therapy desired. However, in general, satisfactory results are obtained when administered at a daily dosage of from 0.05 mg of about 50 mg per kg animal body weight, conveniently given in divided doses 2 to 4 times a day or in sustained release form. For the larger mammal, the total daily dosage is in the range from about 5 to about 500 mg, and dosage forms suitable for oral administration comprise from about 1 mg to about 250 mg of the compounds admixed with a solid or liquid pharmaceutical carrier or diluent.

The compounds of formula I, wherein $R_2$ is halogen, exhibit especially interesting anti-psychotic and neuroleptic activity and the compound of Example 6 has been found to exhibit particularly interesting anti-psychotic and neuroleptic activity at doses of from 1 to 5 mg/kg p.o. in mice.

The compounds of formula I are also useful as sleep-promoting and sleep-inducing agents as indicated by their activity in the above-mentioned tests and also by their significant effect on the sleep phases of rats, in particular by a significant increase of the deep sleep phase, on administration p.o. of from about 0.1 to about 10 mg/kg animal body weight of the compounds using the method of Stille et al (Psychopharmacologia 28, 325-377 [1973]).

For this use the dosage will, of course, vary depending on the compound employed, mode of administration and therapy desired. However, in general, satisfactory results are obtained when administered at a daily dosage of from 0.01 mg to about 50 mg per kg animal body weight, conveniently given in a single dose shortly before the time when sleep is required. For the larger mammal, the total daily dosage is in the range from about 1 to about 100 mg.

The compounds of formula I, wherein $R_2$ is hydrogen, exhibit especially interesting sleep-promoting and sleep-inducing activity. In particular, the compound of Example 2 exhibits particularly useful activity when administered p.o. at a dose of from about 1 to about 5 mg/kg to a rat.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent. Such compositions may be in the form of, for example, a solution or a tablet.

Further suitable acids for salt formation include malonic, malic and tartaric acids.

What is claimed is:

1. A compound of formula I,

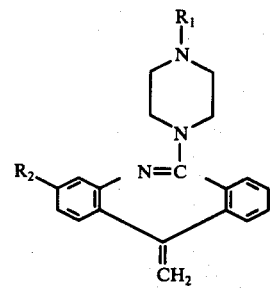

wherein
 $R_1$ is hydrogen, alkyl of 1 to 4 carbon atoms, or hydroxyalkyl of 1 to 4 carbon atoms, and
 $R_2$ is hydrogen or halogen,
in free base form or in pharmaceutically acceptable acid addition salt form.

2. A compound of claim 1, which is 11-methylene-6-(4-methylpiperazin-1-yl)-morphanthridine.

3. A compound of claim 1, wherein $R_1$ and $R_2$ are respectively H and H.

4. A compound of claim 1, wherein $R_1$ and $R_2$ are respectively HO—CH$_2$—CH$_2$— and H.

5. A compound of claim 1, wherein $R_1$ and $R_2$ are respectively HO—CH$_2$—CH$_2$— and Cl.

6. A compound of claim 1, wherein $R_1$ and $R_2$ are respectively H and Cl.

7. A compound of claim 1, wherein $R_1$ and $R_2$ are respectively CH$_3$ and Cl.

8. A compound of claim 1, wherein $R_1$ and $R_2$ are respectively H and F.

9. A compound of claim 1, wherein $R_1$ and $R_2$ are respectively CH$_3$ and F.

10. A pharmaceutical composition comprising a compound of claim 1 in association with a pharmaceutical carrier or diluent.

11. A method of treating neuroses and psychoses in animals which comprises administering a therapeutically effective amount of a compound of claim 1 to an animal in need of such treatment.

12. A method of promoting or inducing sleep in animals which comprises administering a therapeutically effective amound of a compound of claim 1 to an animal in need of such treatment.

* * * * *